United States Patent
Hashimoto et al.

(10) Patent No.: US 10,842,578 B2
(45) Date of Patent: Nov. 24, 2020

(54) ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe-Shi (JP)

(*) Notice: Subject to any disclaimer, the term of this patent is extended or adjusted under 35 U.S.C. 154(b) by 369 days.

(21) Appl. No.: 15/755,218

(22) PCT Filed: Jun. 24, 2016

(86) PCT No.: PCT/JP2016/003069
§ 371 (c)(1),
(2) Date: Feb. 26, 2018

(87) PCT Pub. No.: WO2017/033381
PCT Pub. Date: Mar. 2, 2017

(65) Prior Publication Data
US 2018/0250830 A1    Sep. 6, 2018

(30) Foreign Application Priority Data

Aug. 25, 2015 (JP) .................................. 2015-165479

(51) Int. Cl.
*A61B 34/37* (2016.01)
*G05B 19/418* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ... B25J 19/04; B25J 9/126; B25J 19/02; B25J 19/06; B25J 11/005; B25J 9/1661;
(Continued)

(56) References Cited

U.S. PATENT DOCUMENTS 4,302,138 A * 11/1981 Zarudiansky .............. B25J 3/04
                                                     414/5
5,447,403 A *  9/1995 Engler, Jr. ........... B25J 15/0009
                                                     294/111
(Continued)

FOREIGN PATENT DOCUMENTS

CN      204997657 U    1/2016
CN      105328700 A    2/2016
(Continued)

OTHER PUBLICATIONS

Shimoga. Institute of Electrical and Electronics Engineers "A Survey of Perceptual Feedback Issues in Dexterous Telemanipulation: Part II. Finger Touch Feedback." Sep. 18, 1993, pp. 274-279.
(Continued)

*Primary Examiner* — Bhavesh V Amin
(74) *Attorney, Agent, or Firm* — Oliff PLC

(57) ABSTRACT

A robot system includes a robot including a tactile sensor and a hand having the tactile sensor, a tactile information generator configured to generate tactile information defined by a pressure distribution based on pressures detected by a plurality of pressure sensors and spatial positions of the plurality of pressure sensors, and output the tactile information, a manipulator configured to make an operator sense the pressure distribution according to the tactile information outputted from the tactile information generator, and when the operator manipulates the manipulator, output manipulating information according to the manipulation, and a robot controller configured to control operation of the hand
(Continued)

of the robot according to the manipulating information outputted from the manipulator.

8 Claims, 14 Drawing Sheets

(51) Int. Cl.
| | |
|---|---|
| B25J 9/00 | (2006.01) |
| B23P 19/04 | (2006.01) |
| B25J 13/00 | (2006.01) |
| B25J 19/04 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ........ B25J 9/1692; G05B 2219/37297; G05B 2219/39102; G05B 2219/40143; G05B 2219/39004; G05B 2219/40182; G05B 2219/40145; G05B 2219/40387; G05B 2219/40139; G05B 2219/40161; G05B 2219/40146; G05B 2219/40627; G05B 2219/39439; G05B 2219/40022; G05B 2219/39531; G05B 2219/40163; G05B 2219/39533; G05B 2219/35464; G05B 2219/40142; G05B 2219/33007; G05B 2219/40169; G05B 2219/40183; G05B 2219/40134; G05B 2219/40195; G05B 2219/40162; G05B 2219/40136; B23P 21/002; B23P 21/00; Y10S 901/09; Y10S 901/47; Y10S 901/08; Y10S 901/03; Y10S 901/27; Y10S 901/41; Y10S 901/10; Y10S 901/46; Y10S 901/02; A61B 34/35; A61B 34/70
See application file for complete search history.

(56) References Cited

U.S. PATENT DOCUMENTS

| | | | | |
|---|---|---|---|---|
| 6,016,385 | A | 1/2000 | Yee et al. | |
| 6,088,017 | A * | 7/2000 | Tremblay | G06F 3/011 345/156 |
| 6,244,644 | B1 * | 6/2001 | Lovchik | B25J 9/104 294/111 |
| 6,517,132 | B2 * | 2/2003 | Matsuda | B25J 15/0009 294/106 |
| 7,370,896 | B2 * | 5/2008 | Anderson | B25J 15/0009 294/106 |
| 7,787,993 | B2 * | 8/2010 | Takahashi | B25J 9/1612 700/262 |
| 8,483,880 | B2 * | 7/2013 | de la Rosa Tames | B25J 15/0009 700/258 |
| 8,574,178 | B2 * | 11/2013 | Tong | A63B 21/4019 601/40 |
| 9,104,271 | B1 * | 8/2015 | Adams | G06F 3/014 |
| 2006/0012197 | A1 * | 1/2006 | Anderson | B25J 15/0028 294/106 |
| 2008/0059138 | A1 * | 3/2008 | Tremblay | G06F 3/011 703/11 |
| 2009/0031825 | A1 * | 2/2009 | Kishida | G01L 5/228 73/862.621 |
| 2009/0120696 | A1 * | 5/2009 | Hayakawa | G06F 3/0414 178/18.05 |
| 2009/0133508 | A1 * | 5/2009 | Johansson | G01L 5/228 73/862.046 |
| 2010/0139437 | A1 * | 6/2010 | Ichikawa | B25J 13/082 74/490.05 |

(56) References Cited

U.S. PATENT DOCUMENTS

| | | | | |
|---|---|---|---|---|
| 2013/0079905 A1* | 3/2013 | Saen | .................. | B25J 9/1671 |
| | | | | 700/83 |
| 2013/0238129 A1* | 9/2013 | Rose | .................. | B25J 9/1612 |
| | | | | 700/258 |
| 2015/0019013 A1* | 1/2015 | Rose | .................. | B25J 15/10 |
| | | | | 700/258 |

FOREIGN PATENT DOCUMENTS

| | | | |
|---|---|---|---|
| JP | 2003-311661 | A | 11/2003 |
| JP | 2007-285784 | A | 11/2007 |
| JP | 2008-176779 | A | 7/2008 |
| JP | 2009-282720 | A | 12/2009 |
| JP | 2013-91114 | A | 5/2013 |
| JP | 2014-145717 | A | 8/2014 |

OTHER PUBLICATIONS

Sep. 27, 2016 International Search Report issued in International Patent Application No. PCT/JP2016/003069.

Feb. 27, 2018 International Preliminary Report on Patentability issued in International Patent Application No. PCT/JP2016/003069.

May 5, 2017 Taiwanese Office Action issued in Taiwanese Patent Application No. 105126884.

* cited by examiner (a)

(b)

(a)

(b)

(a)

(b)

# ROBOT SYSTEM

TECHNICAL FIELD

The present disclosure relates to a robot system.

BACKGROUND ART

Conventionally, robot control systems utilizing tactile are known. For example, a manipulating device which manipulates a mobile robot while obtaining a force feedback between a joystick and the mobile robot, is known (e.g., see Patent Document 1). Moreover, a robot hand provided with a tactile sensor system is known (e.g., see Patent Document 2). Moreover, a pressure-distribution information detecting device which is provided with tactile sensors at a robot hand, and controls the robot hand based on a pressure distribution detected by the tactile sensors, is known.

REFERENCE DOCUMENTS OF CONVENTIONAL ART

Patent Documents

[Patent Document 1] JP2009-282720A
[Patent Document 2] JP2014-145717A

DESCRIPTION OF THE DISCLOSURE

Problems to be Solved by the Disclosure

However, such conventional technologies still have room for an improvement in terms of practicality.

One purpose of the present disclosure is to improve practicality of a robot system which remotely controls a robot based on tactile information defined by a pressure distribution.

SUMMARY OF THE DISCLOSURE

The present inventors have diligently examined the problems described above in order to solve them. The present inventors have focused on a work to be performed by a human not utilizing "force sensation" that is merely a force or pressure, but utilizing essential "tactile," i.e., a pressure distribution which the human's hand senses. Such a work may be, for example, a work to scoop up soil by hand, a work to grip a bar-shaped member by hand, etc. Thus, the present inventors came up with an idea to make a hand of the robot perform such a work.

Meanwhile, the manipulating device disclosed in Patent Document 1 controls using the "force sensation," but does not use the essential "tactile." The robot hand disclosed in Patent Document 2 uses the "tactile" defined by the pressure distribution, but it is difficult to control the operation of the robot hand exactly like the human performs the work because the operation of the robot hand is controlled by an arithmetic processing part based on detection outputs of the tactile sensors. Since also in the pressure-distribution information detecting device disclosed in Patent Document 3, a behavior control device controls the operation of the robot hand based on the pressure distribution detected by the tactile sensors similar to the robot hand disclosed in Patent Document 2, it is difficult to control the operation of the robot hand exactly like the human performs the work.

Thus, the present inventors have arrived at that the human judges operation to be performed by the robot hand based on detection outputs of the tactile sensors provided to the robot hand, and instructs exact operation to the robot hand. Therefore, the operation of the robot hand is able to be controlled exactly like the human performs the work.

Thus, a robot system according to one aspect of the present disclosure includes a robot including a tactile sensor having a plurality of pressure sensors disposed at mutually different spatial positions, and a hand having the tactile sensor, a tactile information generator configured to generate tactile information defined by a pressure distribution based on pressures detected by the plurality of pressure sensors and spatial positions of the plurality of pressure sensors, and output the tactile information, a manipulator configured to make an operator sense the pressure distribution according to the tactile information outputted from the tactile information generator, and when the operator manipulates the manipulator, output manipulating information according to the manipulation, and a robot controller configured to control operation of the hand of the robot according to the manipulating information outputted from the manipulator.

According to this configuration, when the tactile sensor having the plurality of pressure sensors arranged at mutually different spatial positions detects an object at the hand of the robot, the tactile information generator generates the tactile information defined by the pressure distribution based on the pressures detected by the plurality of pressure sensors and the spatial positions of the plurality of pressure sensors, and outputs the tactile information. Then, the manipulator makes the operator sense the pressure distribution according to the tactile information outputted from the tactile information generator. The operator grasps the tactile detected by the tactile sensor from the pressure distribution and, based on the grasped tactile, operates the manipulator to manipulate the robot so that the robot performs a suitable work. Then, the manipulator outputs the manipulating information corresponding to the manipulation to the robot controller, and the robot controller controls the operation of the hand of the robot according to the manipulating information. Thus, the operator judges the operation to be performed by the hand of the robot based on the detection output of the tactile sensor which the hand of the robot has. Since exact operation is able to be instructed to the hand of the robot, the operation of the hand of the robot is controllable exactly like the human performing the work. As a result, a practicality of the robot system in which the robot is remotely controlled based on the tactile information defined by the pressure distribution is improved.

The manipulator may include a manipulator body being operated by the operator, a plurality of mechanical stimulators, provided to the manipulator body corresponding to the plurality of pressure sensors, and configured to give a mechanical stimulation distribution according to the pressure distribution defining the tactile information outputted from the tactile information generator, to the hand of the operator who manipulates the manipulator, and a manipulation detector configured to detect the manipulation to the manipulator body, and output the detected manipulation as the manipulating information.

According to this configuration, since the manipulator includes the manipulator body being operated by the operator and the plurality of mechanical stimulators provided to the manipulator body corresponding to the plurality of pressure sensors give the mechanical stimulation distribution according to the pressure distribution defining the tactile information outputted from the tactile information generator, to the hand of the operator who manipulates the manipulator, the operator is able to grasp the tactile detected by the tactile sensor based on the mechanical stimulation distribution. Meanwhile, since the manipulation detector detects the manipulation to the manipulator body and outputs the detected manipulation as the manipulating information, the operator is able to instruct the exact operation to the hand of the robot while grasping the tactile detected by the tactile sensor, only by the manipulator.

The plurality of mechanical stimulators may be a plurality of pressing elements configured to give a pressing-force distribution according to the pressure distribution defining the tactile information outputted from the tactile information generator, to the hand of the operator who manipulates the manipulator.

According to this configuration, since the plurality of pressing elements give the pressing-force distribution according to the pressure distribution defining the tactile information, to the hand of the operator, the operator is able to instinctively grasp the pressure distribution detected by the plurality of pressure sensors through the tactile information.

The pressing element may be a piezo-electric element.

According to this configuration, the pressing element can suitably be configured.

The plurality of mechanical stimulators may be a plurality of oscillators configured to give an oscillating distribution according to the pressure distribution defining the tactile information outputted from the tactile information generator, to the hand of the operator who manipulates the manipulator.

According to this configuration, since the plurality of oscillators give the oscillating distribution according to the pressure distribution defining the tactile information, to the hand of the operator, it is easier for the operator to distinguish parts of the hand where forces are acted, compared with the case where the mechanical stimulations which the hand received are, for example, simply the pressing forces.

The manipulator body of the manipulators may be a glove being worn by the operator.

According to this configuration, since the manipulator body can be configured by the glove corresponding to either one of the left and right hands of the robot, grasping of the tactile detected by the tactile sensor and the operational instruction to the hand of the robot can suitably be performed by one hand.

The manipulation detector may include a displacement sensor provided to the manipulator body of the manipulator, and may be configured to detect the manipulation to the manipulator body based on a displacement of the manipulator body detected by the displacement sensor.

According to this configuration, the manipulation to the manipulator body can suitably be detected.

Effect of the Disclosure

The present disclosure is configured as described above, and it is capable of improving the practicality of the robot system which remotely controls the robot based on the tactile information defined by the pressure distribution.

MODES FOR CARRYING OUT THE DISCLOSURE

Figure 1:
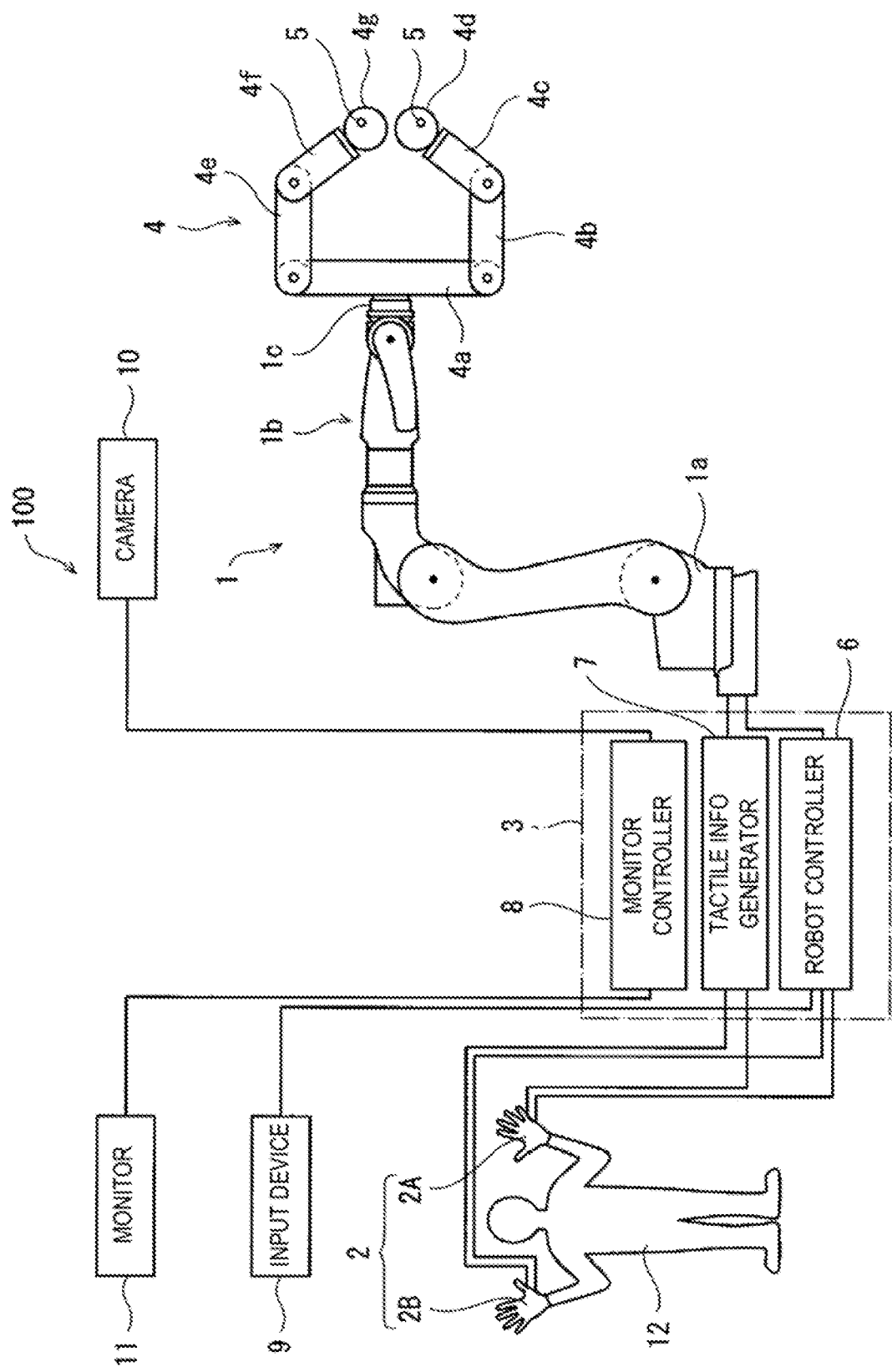
FIG. 1 is a schematic diagram illustrating one example of a configuration of a robot system according to Embodiment 1 of the present disclosure.

Hereinafter, embodiments of the present disclosure will be described with reference to the accompanying drawings. Note that, below, throughout the figures, the same reference characters are given to the same or corresponding elements to omit redundant description.

Embodiment 1

[Configuration]

FIG. 1 is a schematic diagram illustrating one example of a configuration of a robot system according to Embodiment 1 of the present disclosure.

Referring to FIG. 1, a robot system 100 of Embodiment 1 includes a robot 1, a manipulator 2, a control device 3, tactile sensors 5, an input device 9, a camera 10, and a monitor 11. The robot 1 may be comprised of any type of robot. In Embodiment 1, the robot 1 is comprised of, for example, a well-known articulated robot, and includes a pedestal 1a, an articulated arm 1b provided to the pedestal 1a, and a wrist 1c provided to a tip end of the arm 1b. The wrist 1c is attached to the arm 1b so as to be rotatable about an extending axis of arm members which constitute a tip-end part of the arm 1b. An arm 4 of a scalar type dual-arm robot is attached to the wrist 1c as an end effector. The arm 4 of the dual-arm robot includes, for example, a common arm member 4a, a right first arm member 4b, a right second arm member 4c, a right hand 4d, a left first arm member 4e, and a left second arm member 4f, and a left hand 4g. The common arm member 4a is attached to the wrist 1c so as to extend along an axis perpendicular to a rotational axis of the wrist 1c.

A base-end part of the right first arm member 4b is attached to one end of the common arm member 4a so as to be rotatable about an axis which is perpendicular to the rotational axis of the wrist 1c and an axis perpendicular to the rotational axis of the wrist 1c. A base-end part of the right second arm member 4c is attached to the other end of the right first arm member 4b so as to be rotatable about an axis parallel to the rotational axis of the right first arm member 4b. A base-end part of the right hand 4d is attached to a tip end of the right second arm member 4c so as to be rotatable about an axis perpendicular to a rotational axis of the right second arm member 4c.

Moreover, a base-end part of the left first arm member 4e is attached to the other end of the common arm member 4a so as to be rotatable about an axis perpendicular to the rotational axis of the wrist 1c and an axis perpendicular to the rotational axis of the wrist 1c. A base-end part of the left second arm member 4f is attached to the other end of the left first arm member 4e so as to be rotatable about an axis parallel to the rotational axis of the left first arm member 4e. A base-end part of the left hand 4g is attached to a tip end of the left second arm member 4f so as to be rotatable about an axis perpendicular to the rotational axis of the left second arm member 4f.

Each of the members 4a to 4g is driven while being position-controlled by servo motors (not illustrated). Thus, the robot 1 is capable of moving each of the right hand 4d and the left hand 4g in any directions with any postures.

The control device 3 includes a robot controller 6, a tactile information generator 7, and a monitor controller 8. The control device 3 is comprised of a device having arithmetic processing capabilities, such as a computer, a microcontroller, or a microprocessor. The robot controller 6, the tactile information generator 7, and the monitor controller 8 are implemented by an arithmetic processing part (not illustrated) of the control device 3 executing a given program stored in a memory part (not illustrated) of the control device 3. The hardware configuration of the control device 3 is arbitrary, and the control device 3 may be provided independently from other devices of the robot 1 etc., or may be provided integrally with other devices.

The input device 9 is comprised of a man-machine interface, such as a touch panel and/or a keyboard. The input device 9 is mainly used in order to input various data etc. The information inputted into the input device 9 is transmitted to the robot controller 6.

The camera 10 is provided so as to be able to image operation of the robot 1 within part or all of a movable range of the robot 1. The image information imaged by the camera 10 is transmitted to the monitor controller 8. The monitor controller 8 controls the monitor 11 to display an image corresponding to the image information.

A tactile sensor 5 is provided to each of the right hand 4d and the left hand 4g. The tactile sensor 5 includes a plurality of pressure sensors 51 (see FIG. 5) at given spatial positions, and transmits pressures detected by the plurality of pressure sensors 51 to the tactile information generator 7, as will be described later.

The tactile information generator 7 generates tactile information defined by a pressure distribution based on the pressures detected by the plurality of pressure sensors 51 and the spatial positions of the plurality of pressure sensors 51, and transmits (outputs) the tactile information to the manipulator 2.

The manipulator 2 is configured so as to make an operator 12 sense the pressure distribution according to the tactile information outputted from the tactile information generator 7, and when the operator 12 manipulates the manipulator 2, output manipulating information according to the manipulation. The concrete configuration of the manipulator 2 will be described later.

The robot controller 6 controls the operation of the robot 1 based on the information inputted into the input device 9 and the manipulating information transmitted from the manipulator 2. Here, those information are suitably stored in the memory part of the control device 3.

By the above configuration, the operator 12 is able to operate the robot 1 as he/she intended by manipulating the manipulator 2 while looking at the monitor 11 and sensing through the tactile information the pressure distribution detected by the tactile sensor 5. Note that, when the operator 12 performs manipulation exceeding the movable range of the robot 1 to the manipulator 2, the operation of the robot 1 is restricted to the movable range.

Figure 2:
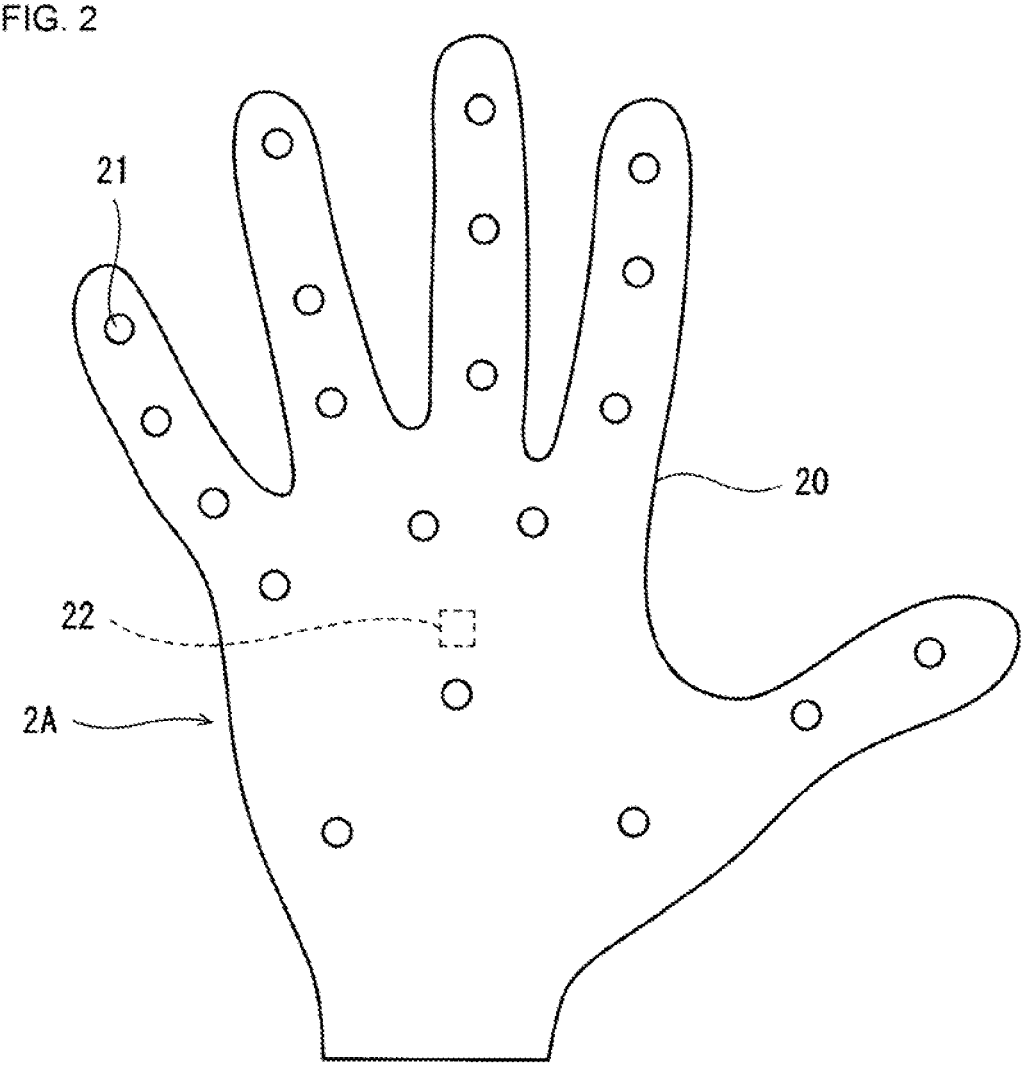
FIG. 2 is a plan view illustrating one example of a configuration of a manipulator glove for the right hand as a manipulator used for the robot system of FIG. 1.
Figure 3:
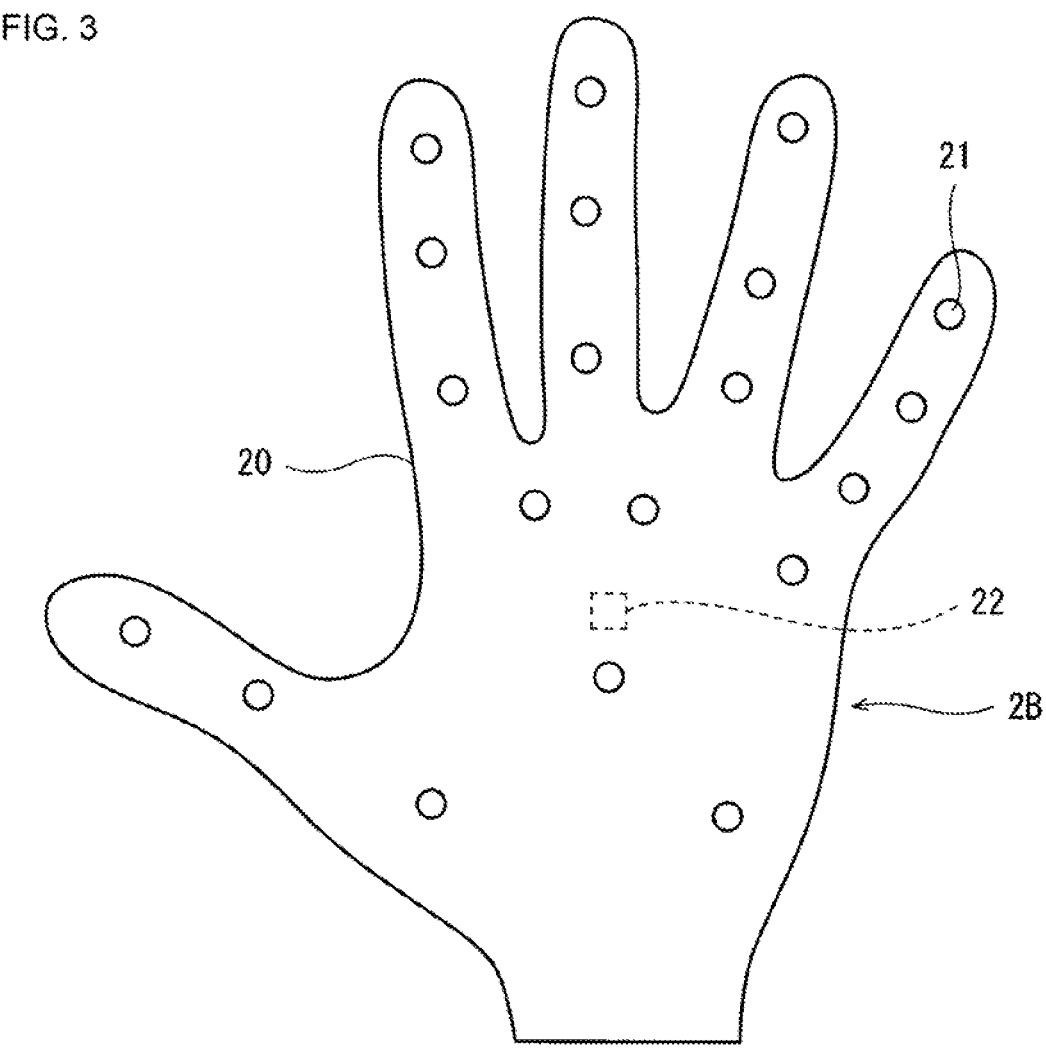
FIG. 3 is a plan view illustrating one example of a configuration of a manipulator glove for the left hand as the manipulator used for the robot system of FIG. 1.

FIG. 2 is a plan view illustrating one example of a configuration of a manipulator glove for the right hand as the manipulator, and FIG. 3 is a plan view illustrating one example of a configuration of a manipulator glove for the left hand.

Referring to FIGS. 2 and 3, the manipulator 2 is comprised of, for example, a manipulator glove 2A for the right hand and a manipulator glove 2B for the left hand, which are worn by the operator 12. Since the manipulator glove 2A for the right hand and the manipulator glove 2B for the left hand are bilaterally symmetrical, only the manipulator glove 2A for the right hand will be described below and description of the manipulator glove 2B for the left hand will be omitted.

The manipulator glove 2A for the right hand includes a glove 20 as a manipulator body which is manipulated by the operator 12, a plurality of pressing elements 21 which are provided to the glove 20 corresponding to the plurality of pressure sensors 51 of the tactile sensor 5 (see FIG. 5), and give to the hand (right hand) of the operator 12 a pressing-force distribution according to the pressure distribution which defines the tactile information outputted from the tactile information generator 7 (see FIG. 1), and a manipulation detector 22 which detects manipulation to the glove 20 and outputs the detected manipulation as the manipulating information. Specifically, the glove 20 is comprised of, for example, cloth formed in the shape of a glove. The kind of cloth is not limited in particular. This cloth may be, for example, a main body of the glove, and it may have a thick base cloth formed in the shape of a glove, and a covering cloth thinner than the base cloth, which covers an inner surface (a surface on the inserted hand side) of the base cloth of the shape of a glove. The pressing elements 21 are disposed, for example, at given positions as illustrated in FIG. 2. Specifically, the plurality of pressing elements 21 are provided to, for example, portions of the glove 20 corresponding to tips of the fingers and the thumb of a person, and palm-side portions between joints, and the palm. Relative positions of the plurality of pressing elements 21 in the glove 20 correspond to relative positions of the plurality of pressure sensors 51 in a main body 41*a* (and 42*a*) of the hand illustrated in FIG. 5. The pressing element 21 is provided on the surface of the base cloth so that a movable part thereof moves forward from the base cloth to the covering cloth and backward. According to the configuration, the movable part of the pressing element 21 moves forward to act a pressing force on the operator's hand. The pressing element 21 may be such that the movable part moves forward and backward according to the pressure detected by the pressure sensor 51. The pressing element 21 may be, for example, a piezoelectric element, or an air cell which inflates and deflate by air supplied and discharged. The tactile information generator 7 transmits the tactile information to the plurality of pressing elements 21 through signal wires (not illustrated).

The manipulation detector 22 is configured to detect the manipulation to the glove 20 based on displacement of the glove as the manipulator body. Specifically, the manipulation detector 22 is comprised of a displacement sensor. The displacement sensor may be an acceleration sensor, a gyroscope sensor, etc. Here, the manipulation detector 22 is comprised of a gyroscope sensor. If it is the gyroscope sensor, the displacement of the glove 20 and a change in the posture are detectable by a single sensor. Here, the manipulation detector 22 is provided to the outside of the glove (back side of the hand) in a central part of the glove 20 in the plan view. The detection output (manipulating information) of the manipulation detector 22 is transmitted to the robot controller 6 through signal wires (not illustrated).

Figure 4:
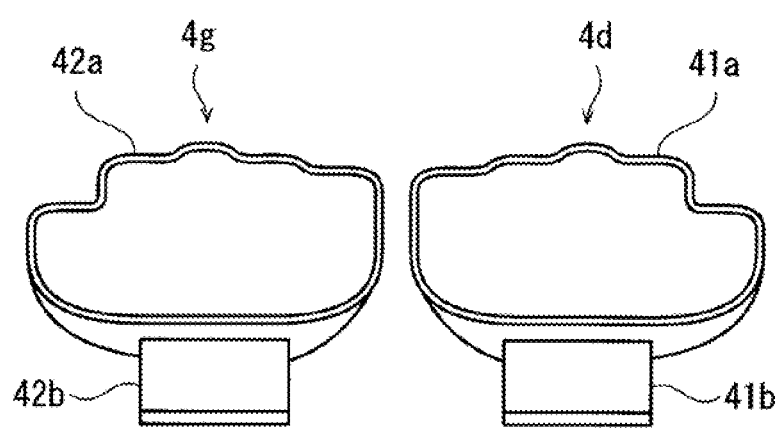
FIG. 4 is a perspective view illustrating one example of a configuration of hands of a robot of FIG. 1.
Figure 5:
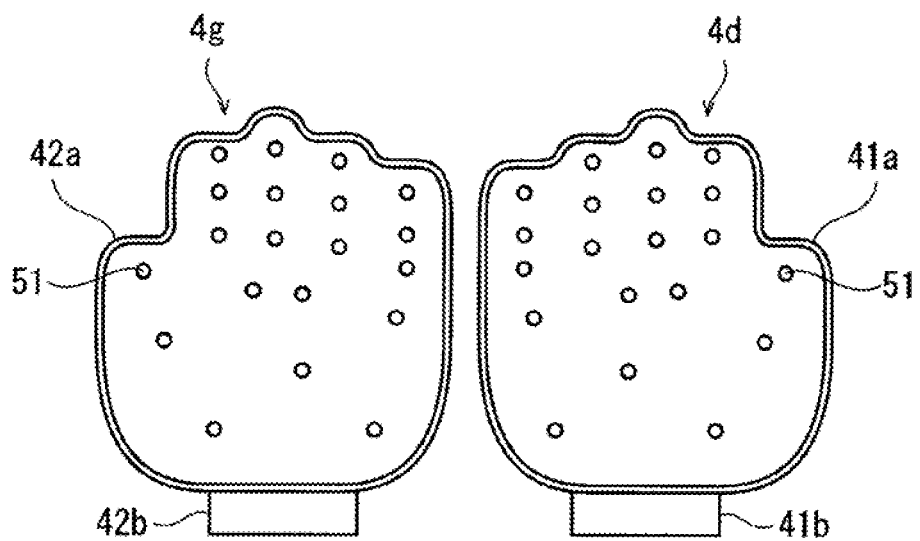
FIG. 5 is a plan view illustrating one example of the configuration of the hands of the robot of FIG. 1.

FIG. 4 is a perspective view illustrating one example of a configuration of hands 4*d* and 4*g*. FIG. 5 is a plan view illustrating one example of the configuration of the hands 4*d* and 4*g*.

Referring to FIGS. 4 and 5, the right hand 4*d* and the left hand 4*g* are configured in the shape which imitates person's hands. Since the right hand 4*d* and the left hand 4*g* are bilaterally symmetrical, only the right hand 4*d* is described below to omit description of the left hand 4*g*. Moreover, in FIG. 4, in order to make the figure intelligible, illustration of the pressure sensors is omitted.

The right hand 4*d* has a main body 41*a* and an attaching part 41*b*. The main body 41*a* is formed entirely in the shape of a shallow container, and the contour of an opening thereof is formed in the shape imitating a person's hand. This is for clarifying a correspondence relation with the manipulator glove 2A. Note that the shape of the opening is arbitrary as long as it is designed so that the correspondence relation is clear. For example, it may be a circle. The attaching part 41*b* for attaching the main body 41*a* to the tip end of the right second arm member 4*c* is provided to a base-end part of the main body 41*a*. The attaching part 41*b* is attached to the tip end of the right second arm member 4*c* so as to be rotatable through a rotating mechanism (not illustrated).

Referring to FIG. 5, the plurality of pressure sensors 51 are provided to the right hand 4*d*. The plurality of pressure sensors 51 are provided so as to protrude from an inner surface of the main body 41*a* at given positions. Specifically, the plurality of pressure sensors 51 are provided, for example, in the main body 41*a*, to portions corresponding to tips of the fingers and thumb of a person, and palm-side portions between joints, and the palm. The relative positions of the plurality of pressure sensors 51 in the main body 41*a* correspond to the relative positions of the plurality of pressing elements 21 in the glove 20 illustrated in FIG. 2.

The pressure sensor 51 may be, for example, a piezoelectric element. The detection outputs of the plurality of pressure sensors 51 are transmitted to the tactile information generator 7 through signal wires (not illustrated).

The positions of the plurality of pressure sensors 51 in the main body 41*a* (and 41*b*) are stored in the memory part (not illustrated) of the control device 3. The tactile information generator 7 described above generates the tactile information defined by the pressure distribution based on the pressures detected by the plurality of pressure sensors 51 disposed in this way, and the positions (spatial positions) of the plurality of pressure sensors 51 in the inner surface of the main body 41*a* which are stored in the memory part of the control device 3.

[Operation]

Next, operation of the robot system 100 configured as described above is described using FIGS. 1 to 7. Here, a work in which the right hand 4*d* and the left hand 4*g* of the robot 1 scoop up soil 60 piled in the shape of a mountain at a given location is described as an example.

Figure 6:
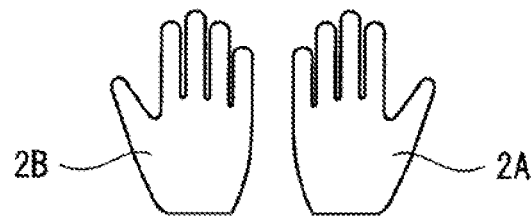
FIGS. 6(a) and (b) are schematic diagrams illustrating a soil-scooping work by the hands of the robot of FIG. 4, where (a) is a perspective view illustrating postures of the manipulators, and (b) is a perspective view illustrating a state where the hands of the robot are scooping up soil.
Figure 6:
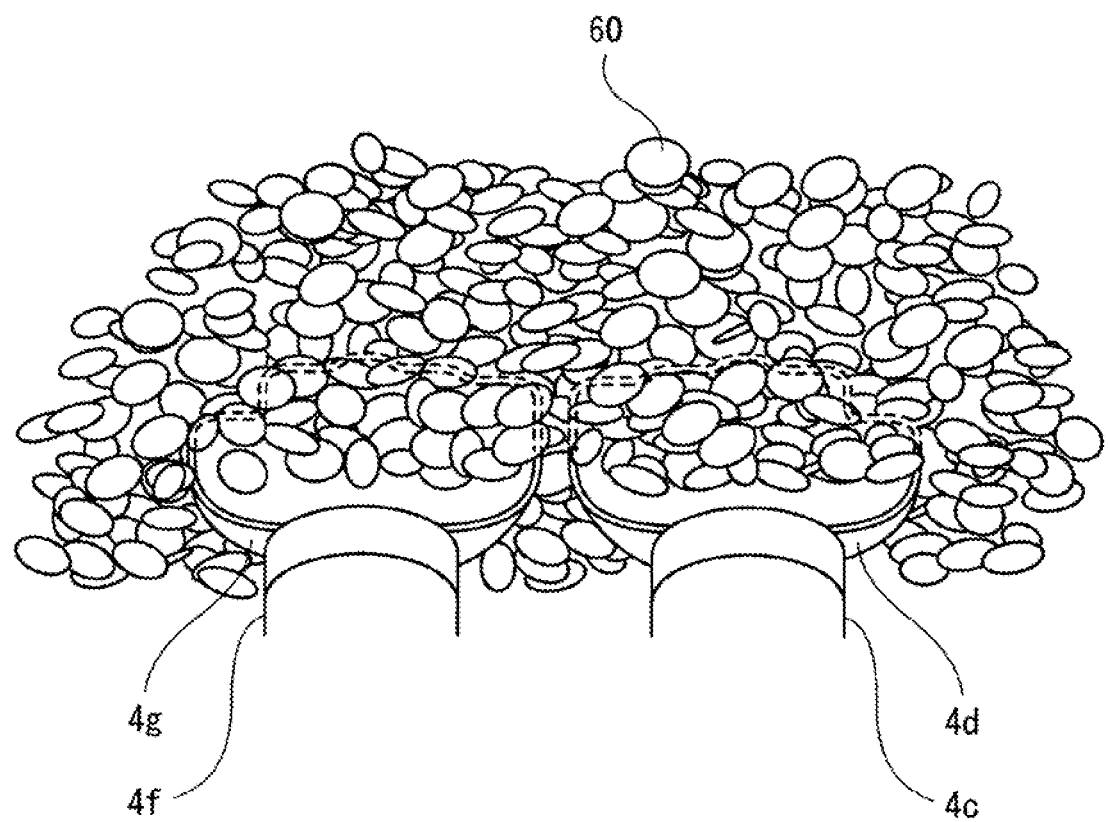
Figure 7:
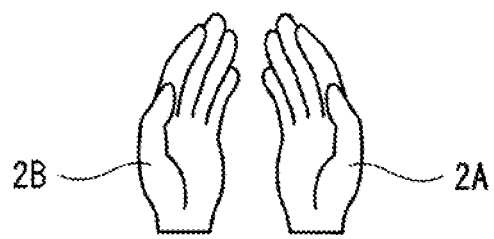
FIGS. 7(a) and (b) are schematic diagrams illustrating the soil-scooping work by the hands of the robot of FIG. 4, where (a) is a perspective view illustrating postures of the manipulators, and (b) is a perspective view illustrating a state where the hands of the robot scooped up soil.
Figure 7:
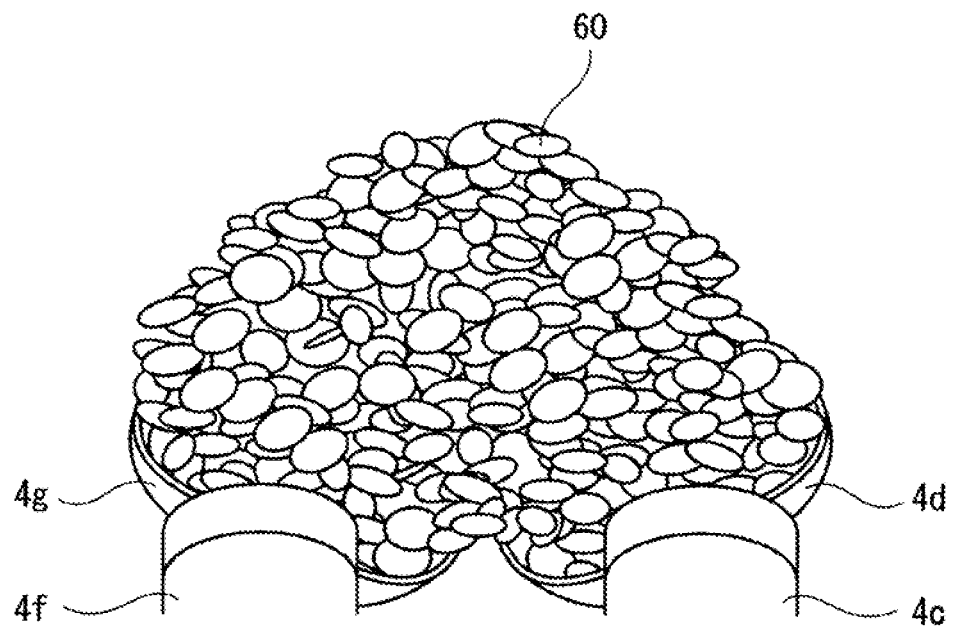

FIGS. 6(*a*) and (*b*) are schematic diagrams illustrating the soil-scooping work by the hands of the robot of FIG. 4, where (a) is a perspective view illustrating postures of the manipulators, and (b) is a perspective view illustrating a state where the hands of the robot are scooping up soil. FIGS. 7(*a*) and (*b*) are schematic diagrams illustrating the soil-scooping work by the hands of the robot of FIG. 4, where (a) is a perspective view illustrating postures of the manipulators, and (b) is a perspective view illustrating a state where the hands of the robot scooped up soil.

The operator 12 wears the manipulator glove 2A for the right hand and the manipulator glove 2B for the left hand on right and left hands, respectively. Then, while looking at the monitor 11, the operator moves the manipulator glove 2A for the right hand and the manipulator glove 2B for the left hand so that the right hand 4*d* and the left hand 4*g* of the robot 1 approaches the soil 60 piled in the shape of a mountain. Then, the respective manipulation detectors 22 detect the movements of the manipulator glove 2A for the right hand and the manipulator glove 2B for the left hand, and transmit the detection outputs as the manipulating information and to the robot controller 6. The robot controller 6 controls the operation of the right hand 4*d* and the left hand 4*g* of the robot 1 according to the manipulating information. Thus, the right hand 4*d* and the left hand 4*g* approach the soil 60 piled in the shape of a mountain.

Next, as illustrated in FIG. 6(*a*), the operator 12 moves the manipulator glove 2A for the right hand and the manipulator glove 2B for the left hand forward away from the operator in a state where the palms are turned upwardly and both hands are put together side by side. Then, the respective manipulation detectors 22 detect the postures and the movements of the manipulator glove 2A for the right hand and the manipulator glove 2B for the left hand, and as a result, the right hand 4*d* and the left hand 4*g* are inserted into the soil 60 piled in the shape of a mountain.

Then, in the right hand 4*d* and the left hand 4*g*, the pressure sensors 51 disposed at portions where the soil are placed detect the pressures, and transmit them to the tactile information generator 7. Then, the tactile information generator 7 generates the tactile information defined by the pressure distribution based on the pressures detected by the pressure sensors 51, and the positions of the pressure sensors 51 (positions in the main body 41a of the right hand 4d and the main body 42a of the left hand 4g), and transmits it to the plurality of pressing elements 21 of the manipulator glove 2A for the right hand and the plurality of pressing elements 21 of the manipulator glove 2B for the left hand.

Then, in the manipulator glove 2A for the right hand and the manipulator glove 2B for the left hand, the movable parts of the pressing elements 21 corresponding to the pressure sensors 51 disposed at the portions where the soil are placed move forward. Thus, since an inner surface of the left hand and an inner surface of the right hand of the operator 12 are pressed by the pressing elements 21, the operator 12 is able to sense where in the right hand 4d and the left hand 4g the soil 60 are placed, and the weight of the placed soil 60.

Then, while the operator sensing that, he/she moves the manipulator glove 2A for the right hand and the manipulator glove 2B for the left hand forward, and when the operator senses that the soil 60 are placed entirely on the right hand 4d and the left hand 4g, stops the manipulator glove 2A for the right hand and the manipulator glove 2B for the left hand, and as illustrated in FIG. 7(a), then leans the manipulator glove 2A for the right hand and the manipulator glove 2B for the left hand inwardly by a slight angle, and then moves the manipulator glove 2A for the right hand and the manipulator glove 2B for the left hand upwardly.

Thus, as illustrated in FIG. 7(b), the right hand 4d and the left hand 4g move upwardly after they are inclined inwardly by the slight angle, and, as a result, the soil 60 are scooped up by the right hand 4d and the left hand 4g. This work is especially effective when the camera 10 is not able to check how much soil 60 are placed on the right hand 4d and the left hand 4g, due to the dead angle of the camera 10 etc.

As described above, according to Embodiment 1, since the operator 12 is able to sense the detection outputs of the tactile sensors 5 which the right hand 4d and the left hand 4g of the robot 1 have through the plurality of pressing elements 21 of the manipulator glove 2A for the right hand and the manipulator glove 2B for the left hand, respectively, the operator 12 is able to judge the operation to be performed by the right hand 4d and the left hand 4g of the robot 1 based on the sense, and instructs exact operation to the right hand 4d and the left hand 4g of the robot 1, the operation of the right hand 4d and the left hand 4g of the robot 1 can be controlled exactly like the human performs the work. As a result, the practicality of the robot system in which the robot 1 is remotely controlled based on the tactile information defined by the pressure distribution is improved.

Embodiment 2

Embodiment 2 of the present disclosure is different from Embodiment 1 in the configuration of the hands of the robot 1, and other configurations are substantially the same as those of Embodiment 1. Hereinafter, the difference is described.

Figure 8:
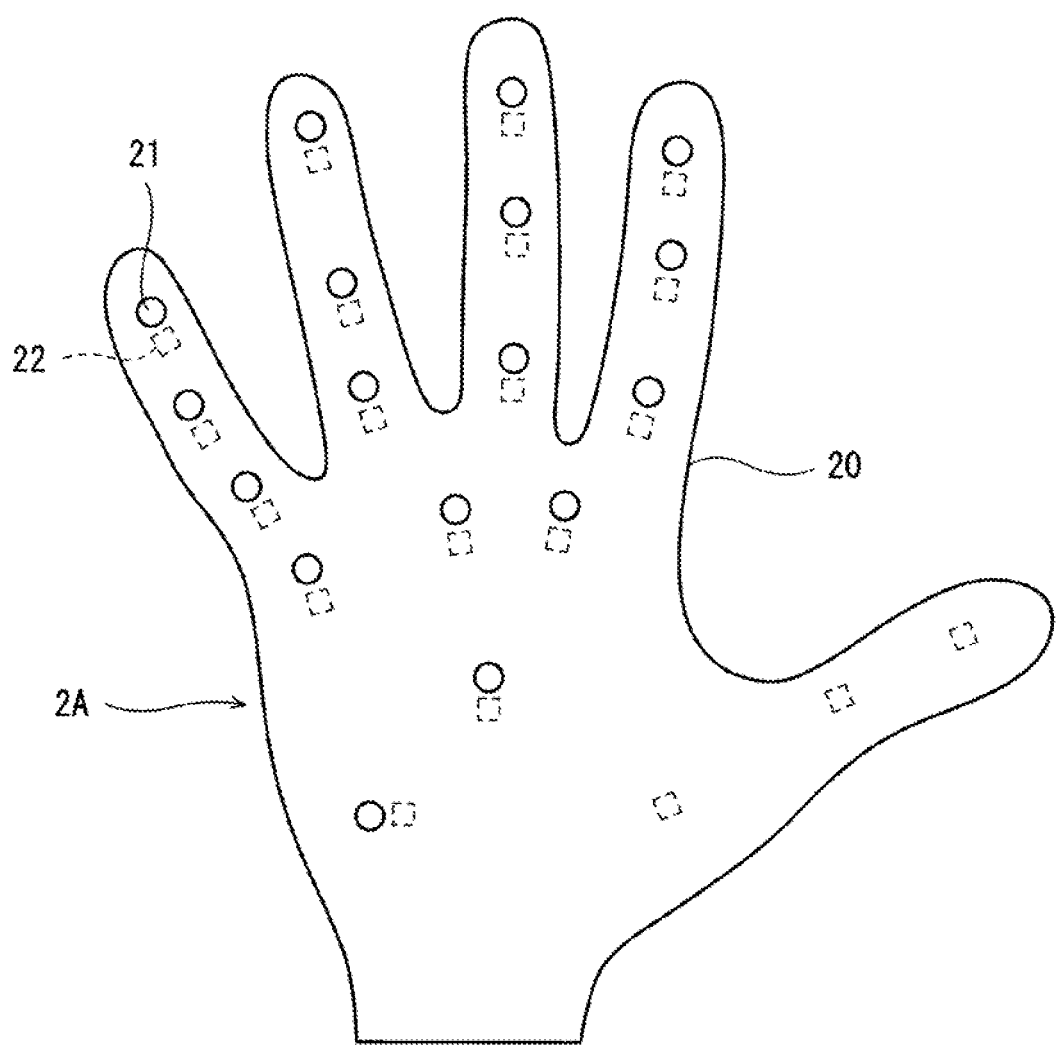
FIG. 8 is a plan view illustrating one example of a configuration of a manipulator glove for the right hand as a manipulator used for a robot system according to Embodiment 2 of the present disclosure.
Figure 9:
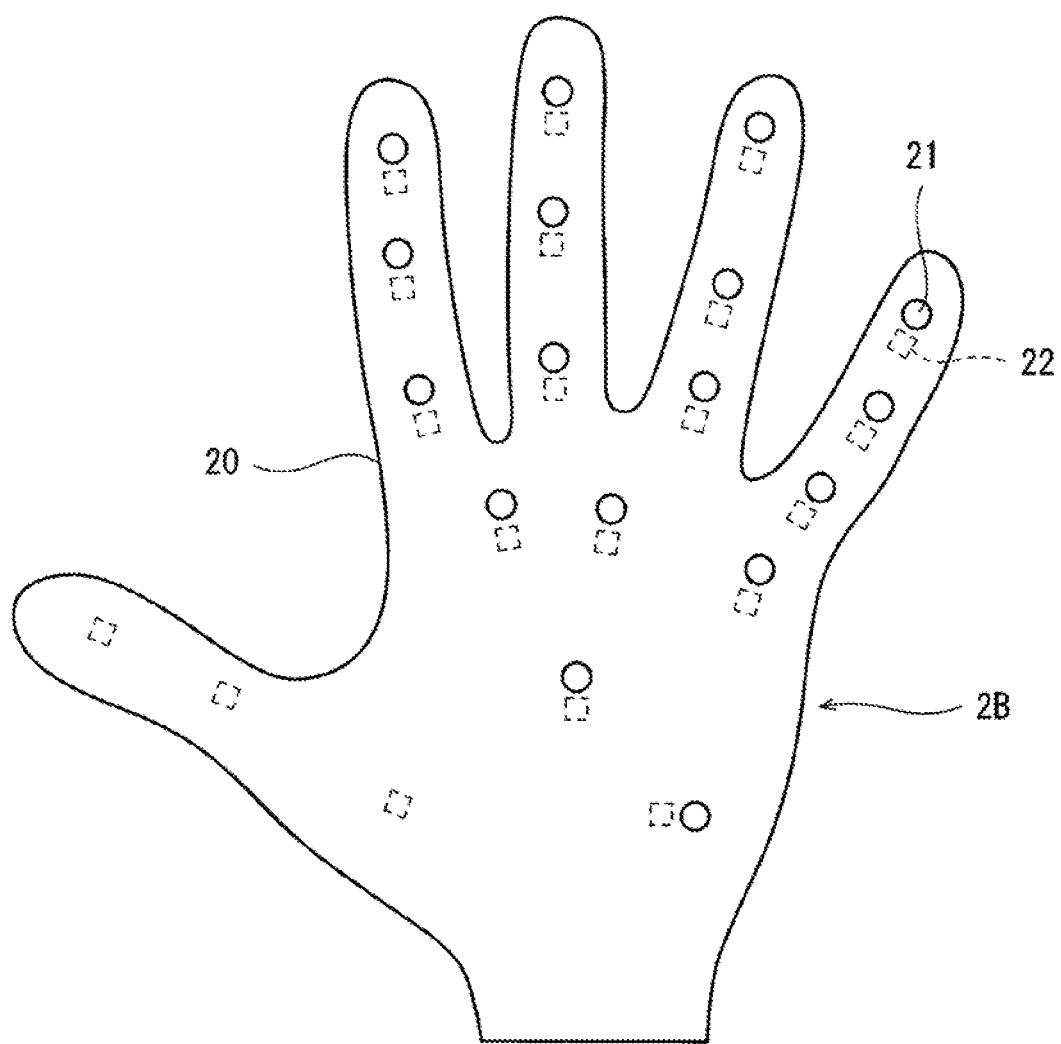
FIG. 9 is a plan view illustrating one example of a configuration of a manipulator glove for the left hand as the manipulator used for the robot system according to Embodiment 2 of the present disclosure.
Figure 10:
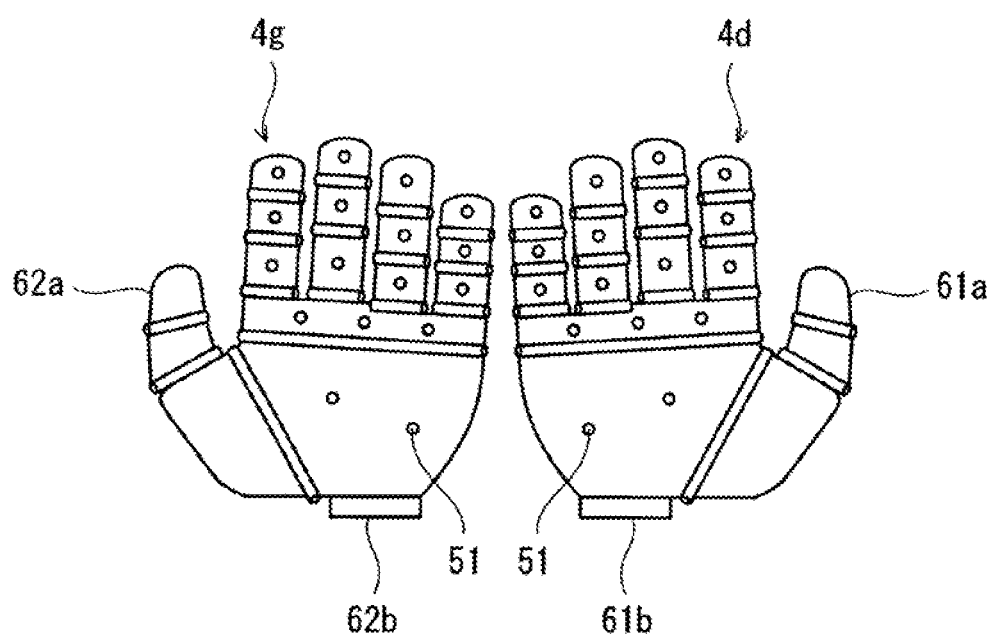
FIG. 10 is a plan view illustrating one example of a configuration of hands of a robot used for the robot system according to Embodiment 2 of the present disclosure.

FIG. 8 is a plan view illustrating one example of a configuration of a manipulator glove for the right hand as a manipulator used for a robot system according to Embodiment 2 of the present disclosure. FIG. 9 is a plan view illustrating one example of a configuration of a manipulator glove for the left hand as the manipulator used for the robot system according to Embodiment 2 of the present disclosure. FIG. 10 is a plan view illustrating one example of a configuration of the hands of the robot used for the robot system according to Embodiment 2 of the present disclosure.

Figure 11:
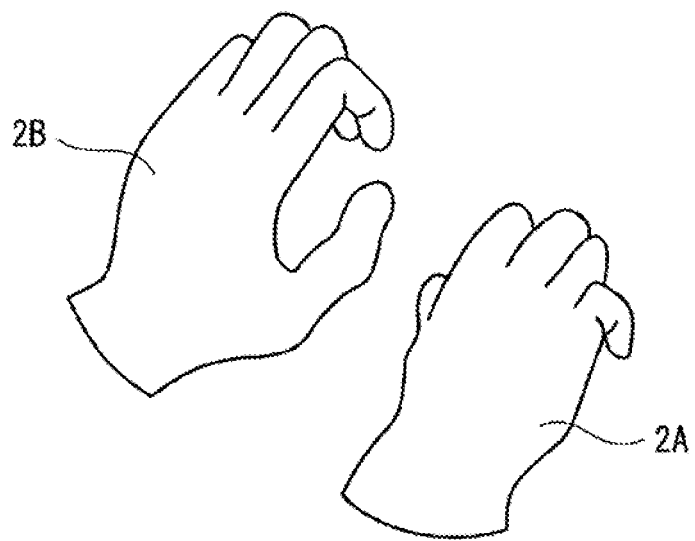
FIGS. 11(a) and (b) are schematic diagrams illustrating a gripping work of a bar-shaped member by the hands of the robot of FIG. 10, where (a) is a perspective view illustrating postures of the manipulators, and (b) is a perspective view illustrating a state where the hands of the robot gripped the bar-shaped member.
Figure 11:
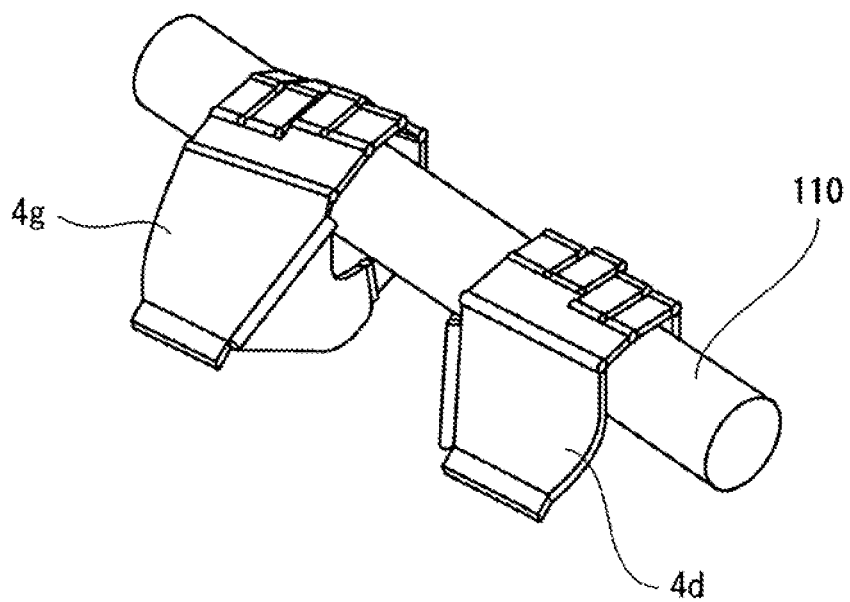

Referring to FIGS. 8 and 9, in Embodiment 2, a plurality of displacement sensors are disposed as the manipulation detectors 22 near the plurality of pressing elements 21, respectively, in the manipulator glove 2A for the right hand and the manipulator glove 2B for the left hand of Embodiment 1 illustrated in FIGS. 2 and 3. Here, the displacement sensor is comprised of an acceleration sensor. This is because that, by providing the plurality of acceleration sensors, each of the postures of the manipulator glove 2A for the right hand and the manipulator glove 2B for the left hand is detectable. Moreover, in Embodiment 2, the pressing elements 21 disposed at the thumb portion are omitted but only the manipulation detectors 22 are disposed at the thumb portion, in the manipulator glove 2A for the right hand and the manipulator glove 2B for the left hand of Embodiment 1 illustrated in FIGS. 2 and 3. That is because that, when gripping a bar-shaped member 110 (see FIG. 11), the pressing elements 21 are unnecessary in the inner surface thereof since the thumb portion contacts the bar-shaped member at the side surface thereof.

Referring to FIG. 10, in Embodiment 2, the right hand 4d and the left hand 4g of the robot 1 are provided with joints corresponding to the joints of person's hands. These joints are driven, for example, while being position-controlled by servo motors. Note that the reference characters 61a and 61b indicate a main body and an attaching part of the right hand 4d, respectively, and the reference characters 62a and 62b indicate a main body and an attaching part of the left hand 4g, respectively.

FIGS. 11(a) and (b) are schematic diagrams illustrating a gripping work of the bar-shaped member 110 by the hands of the robot of FIG. 10, where (a) is a perspective view illustrating postures of the manipulators, and (b) is a perspective view illustrating a state where the hands of the robot gripped the bar-shaped member 110.

According to Embodiment 2, in a state where the right hand 4d and the left hand 4g of the robot 1 are located above the bar-shaped member 110, as illustrated in FIG. 11(a), when the operator 12 manipulates to grip the manipulator glove 2A for the right hand and the manipulator glove 2B for the left hand, the plurality of manipulation detectors 22 of the manipulator glove 2A for the right hand and the manipulator glove 2B for the left hand detect the manipulation, and transmit the manipulating information to the robot controller 6. The robot controller 6 controls the operation of the right hand 4d and the left hand 4g of the robot 1 of the robot 1 according to the manipulating information. Thus, as illustrated in FIG. 11(b), the right hand 4d and the left hand 4g of the robot 1 grip the bar-shaped member 110, respectively. The operator 12 grips the manipulator glove 2A for the right hand and the manipulator glove 2B for the left hand so as to tighten the gripping gradually, while sensing the pressure distribution detected by the plurality of pressure sensors 51 of the right hand 4d and the left hand 4g through the pressing forces of the plurality of pressing elements 21 of the manipulator glove 2A for the right hand and the manipulator glove 2B for the left hand, respectively, and when the sensed pressing forces of the plurality of pressing elements 21 reach a desired pressing force, stops the gripping operation of the manipulator glove 2A for the right hand and the manipulator glove 2B for the left hand. Thus, the right hand 4d and the left hand 4g of the robot 1 grip the bar-shaped member 110 with suitable pressures.

Therefore, also according to Embodiment 2, the operations of the right hand 4d and the left hand 4g of the robot 1 are controllable exactly like the human performs the work, and as a result, the practicality of the robot system 100 in which the robot 1 is remotely controlled based on the tactile information defined by the pressure distribution is improved.

Embodiment 3

Figure 12:
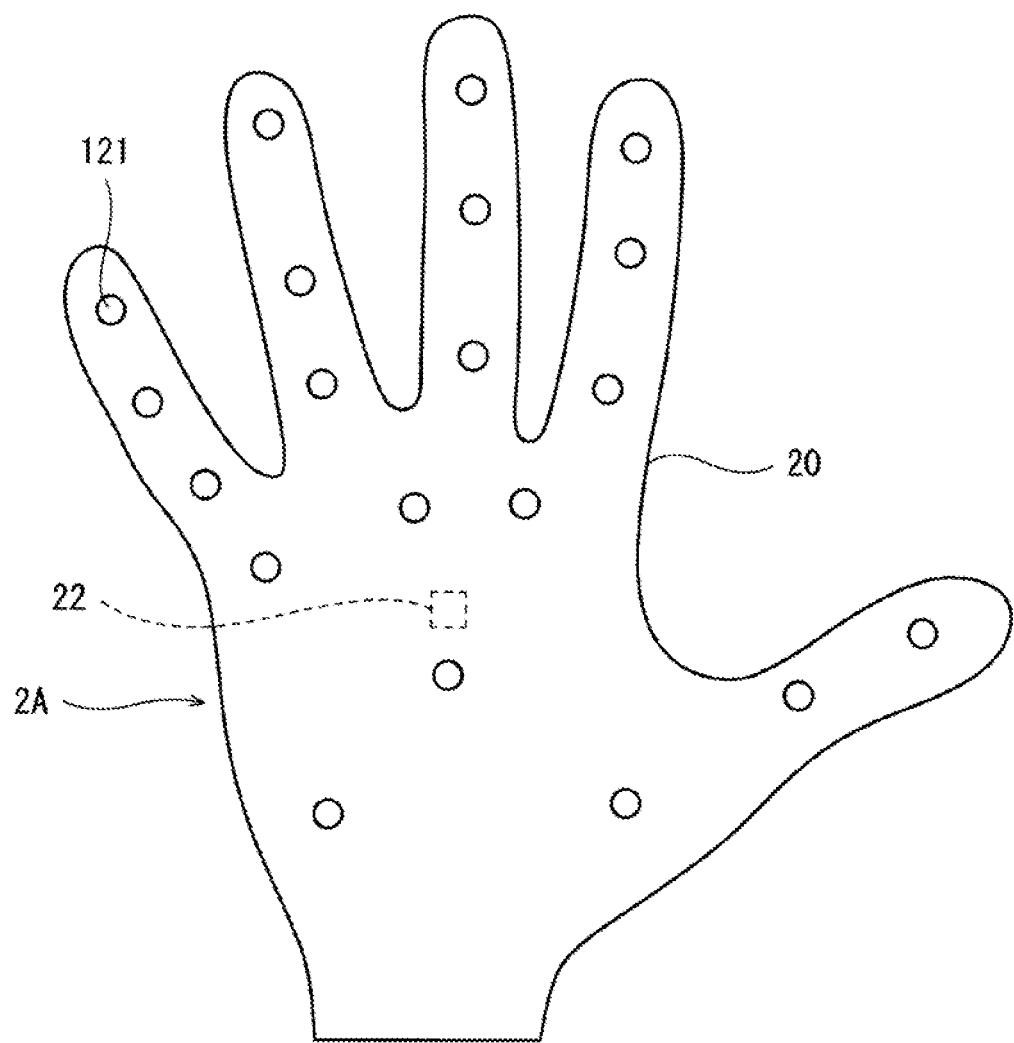
FIG. 12 is a plan view illustrating one example of a configuration of a manipulator glove for the right hand as a manipulator used for a robot system according to Embodiment 3 of the present disclosure.
Figure 13:
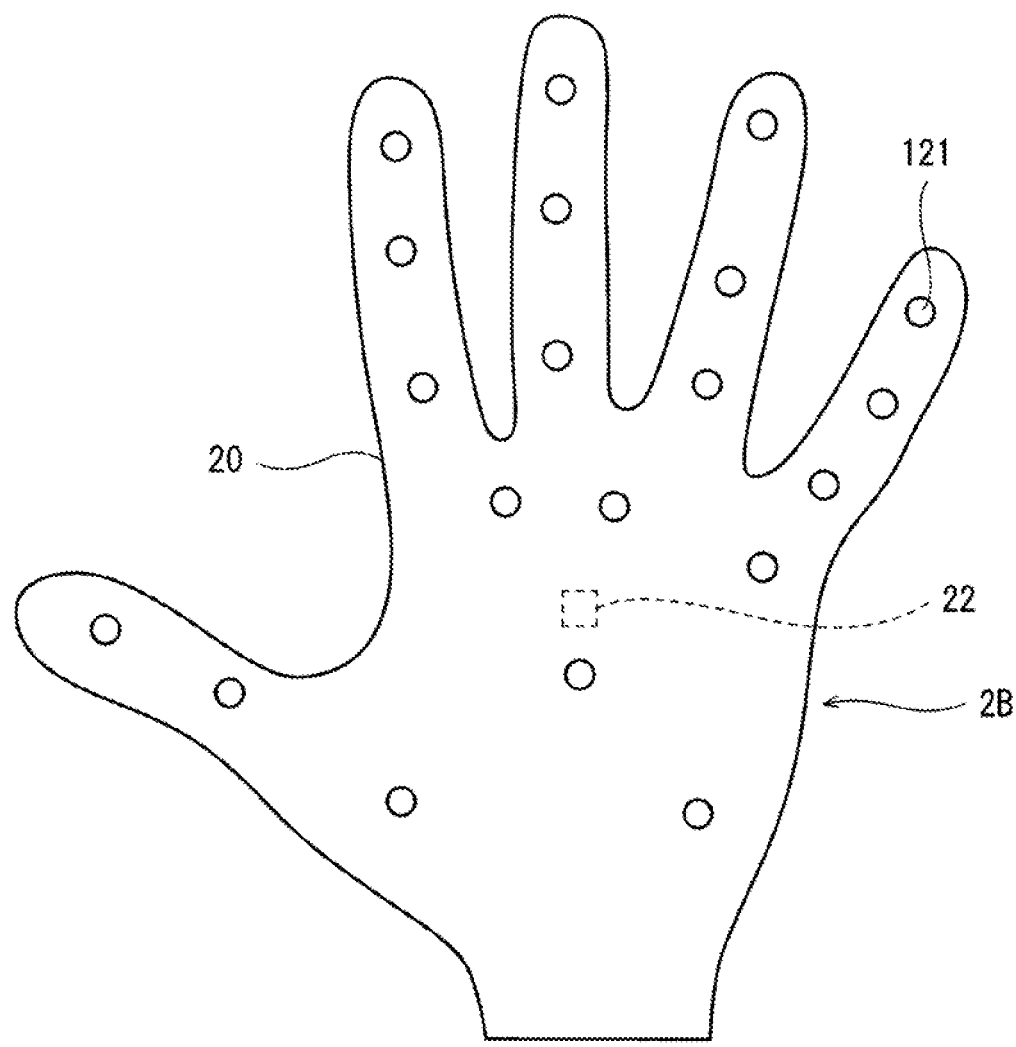
FIG. 13 is a plan view illustrating one example of a configuration of a manipulator glove for the left hand as the manipulator used for the robot system according to Embodiment 3 of the present disclosure.

FIG. 12 is a plan view illustrating one example of a configuration of a manipulator glove for the right hand as a manipulator used for a robot system according to Embodiment 3 of the present disclosure. FIG. 13 is a plan view illustrating one example of a configuration of a manipulator glove for the left hand as the manipulator used for the robot system according to Embodiment 3 of the present disclosure.

In Embodiment 3, oscillators (vibrators) 121 are provided in the manipulator glove for the right hand and the manipulator glove for the left hand illustrated in FIGS. 2 and 3, respectively, instead of the pressing elements 21. Other configurations are similar to those of Embodiment 1.

The oscillator 121 vibrates with amplitude according to the pressure detected by the corresponding pressure sensor 51.

According to such Embodiment 3, it is easier for the operator to distinguish the parts of the hands where forces are acted, compared with the case where the mechanical stimulations which the hands received are, for example, simply the pressing forces.

Embodiment 4

Figure 14:
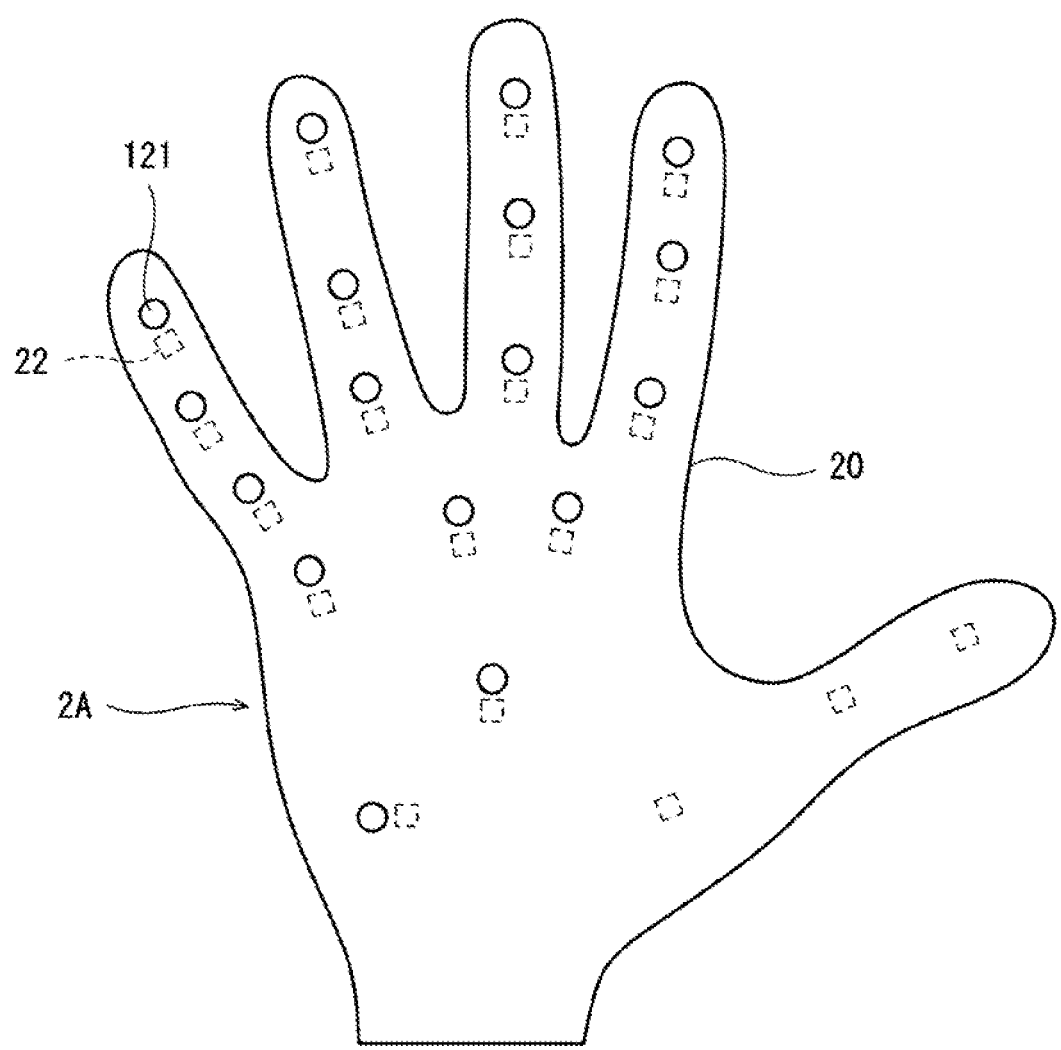
FIG. 14 is a plan view illustrating one example of a configuration of a manipulator glove for the right hand as a manipulator used for a robot system according to Embodiment 4 of the present disclosure.
Figure 15:
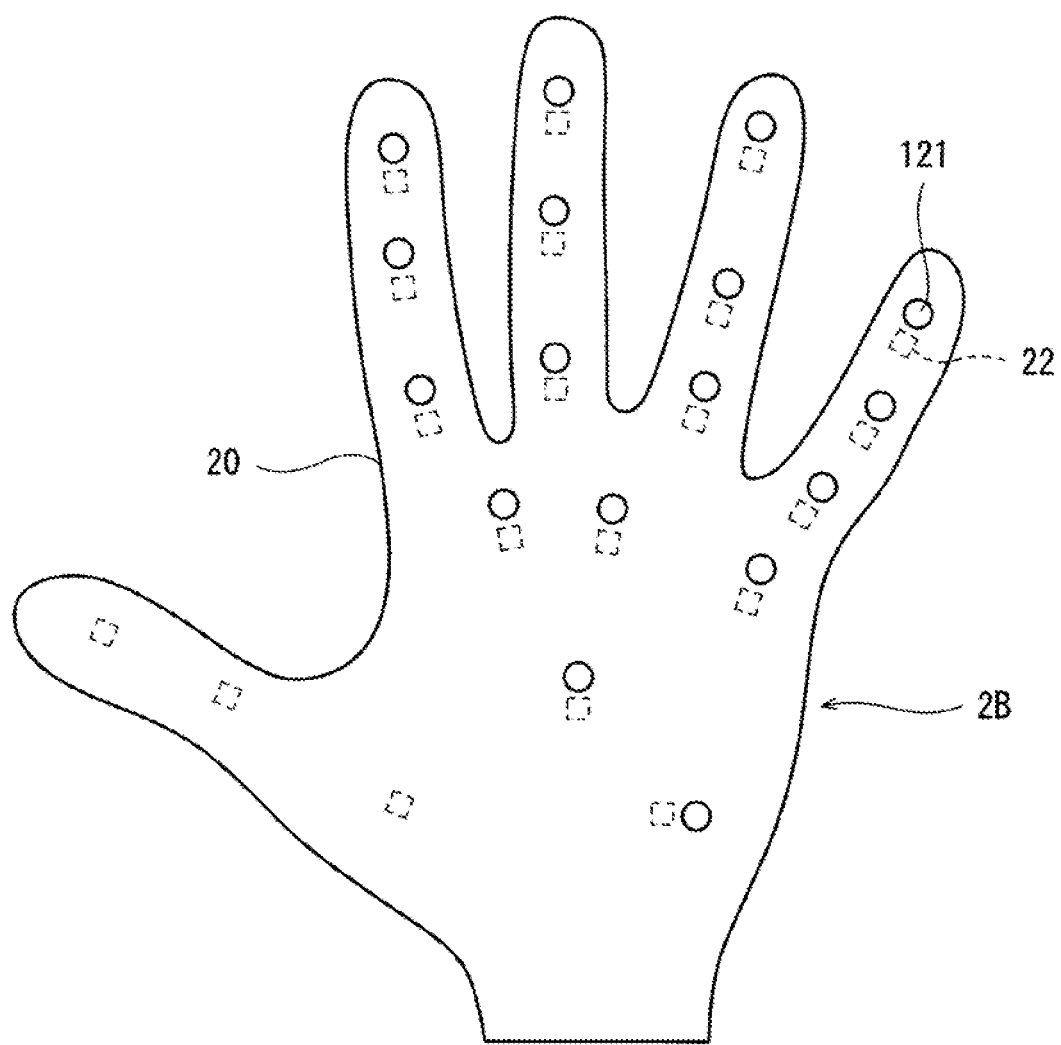
FIG. 15 is plan view illustrating one example of a configuration of a manipulator glove for the left hand as the manipulator used for the robot system according to Embodiment 4 of the present disclosure.

FIG. 14 is a plan view illustrating one example of a configuration of a manipulator glove for the right hand as a manipulator used for a robot system according to Embodiment 4 of the present disclosure. FIG. 15 is a plan view illustrating one example of a configuration of a manipulator glove for the left hand as the manipulator used for the robot system according to Embodiment 4 of the present disclosure.

In Embodiment 4, oscillators (vibrators) 121 are provided in the manipulator glove for the right hand and the manipulator glove for the left hand illustrated in FIGS. 8 and 9, respectively, instead of the pressing elements 21. Other configurations are similar to those of Embodiment 2.

The oscillator 121 vibrates with amplitude according to the pressure detected by the corresponding pressure sensor 51.

According to such Embodiment 4, it is easier for the operator to distinguish the parts of the hands where forces are acted, compared with the case where the mechanical stimulations which the hands received are, for example, simply the pressing forces.

Other Embodiments

In any of Embodiments 1 to 4 described above, the robot 1 may be comprised of a dual-arm robot, for example.

Alternatively, in any of Embodiments 1 to 4 described above, the right hand 4d and the left hand 4g of the robot 1 may also be configured suitable for works.

Alternatively, in any of Embodiments 1 to 4 described above, the manipulator body may be other than the glove. For example, it may be a fingerstall or thumbstall.

It is apparent for a person skilled in the art that many improvements and other embodiments of the present disclosure are possible from the above description. Therefore, the above description is to be interpreted only as illustration, and it is provided in order to teach a person skilled in the art the best mode that implements the present disclosure. Details of the structures and/or the functions may substantially be changed without departing from the spirit of the present disclosure.

INDUSTRIAL APPLICABILITY

The robot system of the present disclosure is useful as the robot system with improved practicality.

DESCRIPTION OF REFERENCE CHARACTERS

1 Robot
2 Manipulator
2A Manipulator Glove for the Right Hand
2B Manipulator Glove for the Left Hand
3 Control Device
4 Arm of Scalar Type Dual-arm Robot
5 Tactile Sensor
6 Robot Controller
7 Tactile Information Generator
8 Monitor Controller
9 Input Device
10 Camera
11 Monitor
12 Operator
20 Glove
21 Pressing Elements
22 Manipulation Detector
51 Pressure Sensor
60 Soil
100 Robot System
110 Bar-shaped Member
121 Oscillator

What is claimed is:

1. A robot system, comprising:
a robot including a tactile sensor having a plurality of pressure sensors disposed at mutually different spatial positions, and a hand having the tactile sensor;
a tactile information circuitry configured to generate tactile information defined by a pressure distribution based on pressures detected by the plurality of pressure sensors and spatial positions of the plurality of pressure sensors, and output the tactile information;
a manipulator configured to make an operator sense the pressure distribution according to the tactile information outputted from the tactile information circuitry, and when the operator manipulates the manipulator, output manipulating information according to the manipulation; and
a robot controller configured to control operation of the hand of the robot according to the manipulating information outputted from the manipulator, wherein:
the hand of the robot is formed in a shape imitating a person's hand, and
the plurality of pressure sensors are provided to at least a portion of the hand of the robot, the portion corresponding to a palm of the person's hand.

2. The robot system of claim 1, wherein
the manipulator includes:
a manipulator body being operated by the operator;
a plurality of mechanical stimulators, provided to the manipulator body corresponding to the plurality of pressure sensors, and configured to give a mechanical stimulation distribution according to the pressure distribution defining the tactile information outputted from the tactile information circuitry, to a hand of the operator who manipulates the manipulator; and a manipulation sensor configured to detect the manipulation to the manipulator body, and output the detected manipulation as the manipulating information.

3. The robot system of claim 2, wherein the plurality of mechanical stimulators are a plurality of pressing elements configured to give a pressing-force distribution according to the pressure distribution defining the tactile information outputted from the tactile information circuitry, to the hand of the operator who manipulates the manipulator.

4. The robot system of claim 3, wherein the pressing element is a piezo-electric element.

5. The robot system of claim 2, wherein the plurality of mechanical stimulators are a plurality of oscillators configured to give an oscillating distribution according to the pressure distribution defining the tactile information outputted from the tactile information circuitry, to the hand of the operator who manipulates the manipulator.

6. The robot system of claim 2, wherein the manipulator body of the manipulator is a glove being worn by the operator.

7. The robot system of claim 2, wherein the manipulation sensor includes a displacement sensor provided to the manipulator body of the manipulator, and is configured to detect the manipulation to the manipulator body based on a displacement of the manipulator body detected by the displacement sensor.

8. The robot system of claim 1, wherein the at least portion of the hand of the robot, to which the plurality of pressure sensors are provided, includes portions that correspond to:
    tips of fingers and a thumb of the person's hand or tips of the fingers of the person's hand;
    palm-side portions between joints of the fingers and the thumb of the person's hand or between joints of the fingers of the person's hand; and
    the palm of the person's hand.

* * * * *